United States Patent
Gross et al.

(10) Patent No.: US 9,356,888 B2
(45) Date of Patent: May 31, 2016

(54) SYSTEM AND METHOD FOR DISTRIBUTING MEANINGFUL CLINICAL ALERTS

(75) Inventors: Brian David Gross, North Andover, MA (US); Charles Lagor, Ardsley, NY (US); David Warren Weiss, Coral Springs, FL (US); Monroe Wyatt Pattillo, Fort Lauderdale, FL (US); Robert Duane Porterfield, Parkland, FL (US); Redvers Curtis Gosse, Boynton Beach, FL (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 326 days.

(21) Appl. No.: 13/977,019

(22) PCT Filed: Dec. 21, 2011

(86) PCT No.: PCT/IB2011/055858
§ 371 (c)(1),
(2), (4) Date: Jun. 28, 2013

(87) PCT Pub. No.: WO2012/093307
PCT Pub. Date: Jul. 12, 2012

(65) Prior Publication Data
US 2013/0275539 A1   Oct. 17, 2013

Related U.S. Application Data

(60) Provisional application No. 61/532,835, filed on Sep. 9, 2011, provisional application No. 61/429,779, filed on Jan. 5, 2011.

(51) Int. Cl.
*G06F 15/16* (2006.01)
*H04L 12/58* (2006.01)
*H04L 12/18* (2006.01)

(52) U.S. Cl.
CPC ............ *H04L 51/00* (2013.01); *H04L 12/1895* (2013.01); *H04L 12/5855* (2013.01); *H04L 51/14* (2013.01); *H04L 12/586* (2013.01); *H04L 12/5885* (2013.01)

(58) Field of Classification Search
CPC .. H04L 12/587; H04L 51/36; H04L 29/08558
USPC .................................. 709/206, 226, 239, 200
See application file for complete search history.

(56) References Cited

U.S. PATENT DOCUMENTS

| 5,534,851 A | 7/1996 | Russek |
| 6,631,363 B1 * | 10/2003 | Brown et al. .................. 719/318 |

(Continued)

FOREIGN PATENT DOCUMENTS

| WO | 0127759 A2 | 4/2001 |
| WO | 2007065015 A2 | 6/2007 |

OTHER PUBLICATIONS

Geissbuhler, A., et al.; Design of a General Clinical Notification System Based on the Publish-Subscribe Paradigm; 1997; AMIA; pp. 126-130.

*Primary Examiner* — El Hadji Sall

(57) ABSTRACT

A messaging system (100) for routing clinical messages includes an event handler and a standardized protocol (105). The event handler (106) receives one or more inbound messages from one or more event sources (102). The event sources (102) include one or more worklist items. The event handler (106) further stores the worklist items in an event database (198) and generates and communicates outbound messages for one or more worklist items in the event database (198) that need to be acted upon, as determined by one or more rules. The standardized protocol (105) is used to represent the inbound messages and the outbound messages.

15 Claims, 7 Drawing Sheets

(56) References Cited

U.S. PATENT DOCUMENTS

| | | |
|---|---|---|
| 7,684,548 B1 * | 3/2010 | Rodkey et al. .............. 379/88.12 |
| 2001/0051890 A1 * | 12/2001 | Burgess ............................ 705/9 |
| 2005/0143671 A1 | 6/2005 | Hastings et al. |
| 2006/0047538 A1 | 3/2006 | Condurso et al. |
| 2009/0132580 A1 * | 5/2009 | James et al. ................... 707/102 |
| 2010/0088118 A1 * | 4/2010 | Jang et al. ......................... 705/3 |
| 2010/0169114 A1 * | 7/2010 | Henderson et al. ................ 705/2 |
| 2011/0208540 A1 | 8/2011 | Lord et al. |
| 2011/0210853 A1 | 9/2011 | Lord et al. |
| 2011/0276343 A1 | 11/2011 | Lagor et al. |
| 2015/0006088 A1 * | 1/2015 | Eshelman et al. .............. 702/19 |

* cited by examiner

SYSTEM AND METHOD FOR DISTRIBUTING MEANINGFUL CLINICAL ALERTS

CROSS REFERENCE TO RELATED APPLICATIONS

This application is a national filing of PCT application Serial No. PCT/IB2011/055858, filed Dec. 21, 2011, published as WO 2012/093307 A1 on Jul. 12, 2012, which claims the benefit of U.S. provisional application Ser. No. 61/532, 835 filed Sep. 9, 2011 and U.S. provisional application Ser. No. 61/429,779 filed Jan. 5, 2011, both of which are incorporated herein by reference.

The present application relates generally to electronic communications. It finds particular application in routing alerts and messages to clinicians, and will be described with particular reference thereto. However, it is to be understood that it also finds application in other usage scenarios, and is not necessarily limited to the aforementioned application. For example, it finds application in manufacturing, fire, security and other industries.

Clinical decision support applications often deliver generic alerts and/or alerts specific to end devices. For example, monitoring systems may generate generic alerts if a parameter reaches a certain threshold. However, one problem with delivering generic alerts and/or alerts specific to end devices is that such alerts fail to target specific clinicians.

Failing to target specific clinicians often leads to alerts reaching disinterested clinicians or never reaching a clinician who can act upon the content of the alert. For example, a clinician may receive an alert that does not pertain to their clinical role and/or their patient list. Other examples include a clinician receiving an alert while they are off duty and/or unavailable or the alert being sent to a device the clinician is carrying which is physically turned off and/or out of communication range.

Additionally, clinical decision support applications often deliver alerts regardless of their temporal relationship to a workflow and/or the urgency for a patient. For example, an alert indicating a need for a Pneumovax vaccine prior to hospital discharge is temporally premature at a time when the critically ill patient is arriving in an Intensive Care Unit (ICU).

Addressing some of these concerns, there are messaging systems which send alerts to devices and include business logic to take action when target devices fail to acknowledge the alerts. However, these systems must typically be configured for each alert and/or user, which is labor intensive, or are generic based on one or more of event source, user role, and notification device. Furthermore, they do not provide for dynamic and/or complex business logic that is based on worklists for a given user and/or patient.

Moreover, messaging systems often lead to less critical alerts reaching clinicians following critical alerts that occupy the clinicians' time. This can be distracting to the clinicians servicing more severe alerts. Also, messaging systems typically wait a predetermined period of time for a clinician to accept an alert before alerting another clinician. This can increases the amount of time it takes to service the less severe alerts since these alerts are not likely to be rejected and the escalation time must generally lapse.

The present application provides a new and improved system and method for routing alerts and other messages to clinicians, which overcomes the above-referenced problems and others.

In accordance with one aspect, a messaging system for routing clinical messages is provided. The system includes an event handler and a standardized protocol. The event handler receives one or more inbound messages from one or more event sources. The messages include one or more worklist items. The event handler further stores the worklist items in an event database and generates and communicates outbound messages for one or more worklist items in the event database that need to be acted upon, as determined by one or more rules. The standardized protocol is used to represent the inbound messages and the outbound messages.

In accordance with another aspect, a method of routing clinical messages is provided. One or more inbound messages in a standardized protocol are received from one or more event sources. The inbound messages include one or more worklist items. The worklist items are stored in an event database and outbound messages in the standardized protocol are generated and communicated for one or more worklist items in the event database that need to be acted upon, as determined by one or more rules.

In accordance with another aspect, a method of self describing and communicating event information to an event handler is provided. An event notice is received and a message using a standardized protocol is generated. The messages includes event information and one or more worklist items, represented using one or more standardized message properties. The worklist items specify to whom the message is directed and how the message should be routed by the event handler.

In accordance with another aspect, a worklist is maintained per patient and per user. The worklist keeps track of active alerts awaiting response, active work items, and future or scheduled worklist items. The worklist enables the system to prioritize and redirect workflow based on severity of incoming tasks or alerts for a given patient and user context.

In accordance with another aspect, a standardized protocol is utilized to establish desired business logic for routing a message. This allows systems that utilize this protocol to establish a mechanism for an external system to pass the message with an end user context as part of the message and have the end user response passed back to the messaging application, without the application needing to know anything about the end user's status or preferences.

One advantage of the present system and method is that it delivers messages in an intelligent manner.

Another advantage resides in the ability to route alerts and/or messages to specific users and clinical roles.

Another advantage resides in the ability to specify a next escalation step for an alert and/or message within the alert and/or message.

Another advantage resides in the ability keep track of the status of various pending alerts, work tasks, and/or messages.

Another advantage resides in the ability for a consolidated workflow to be supported from a multitude of different systems active for the user or patient.

Another advantage resides in the ability to implement alert and/or message handling rules in a flexible manner, by processing messages compliant with self-describing protocols and by permitting specific business rules locally for systems which do not use the protocol.

Another advantage resides in the ability to define complex escalation steps for alerts and/or messages.

Another advantage resides in the ability to provide user acknowledgment and responses selection outside the native application, and have the responses passed back to the alerting application.

Another advantage resides in the ability to represent escalation steps for alerts and/or messages in a standardized manner.

Another advantage resides in that events are accepted and serviced more quickly.

Another advantage resides in that alarm fatigue and distraction on the part of the staff is reduced.

Another advantage resides in improved safety.

Still further advantages of the present invention will be appreciated to those of ordinary skill in the art upon reading and understand the following detailed description.

The invention may take form in various components and arrangements of components, and in various steps and arrangements of steps. The drawings are only for purposes of illustrating the preferred embodiments and are not to be construed as limiting the invention.

FIG. 1 provides an overview of a messaging system according to aspects of the present disclosure;

Figure 1:
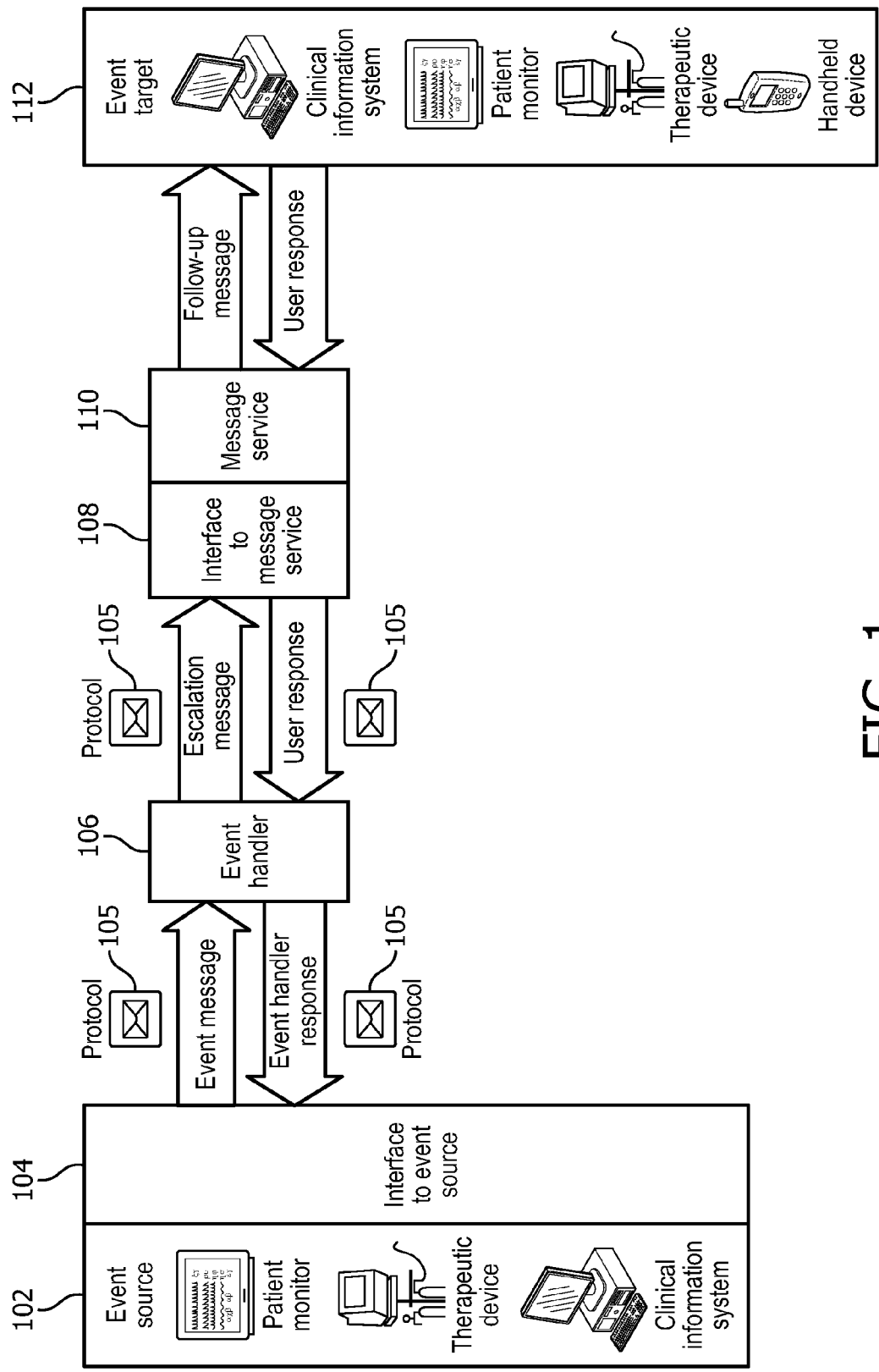

With reference to FIG. 1, in one embodiment, a messaging system 100 includes one or more event source interfaces 104 to one or more event sources 102, an event handler 106, a message service interface 108 to a message service 110 that communicates with one or more event targets 112, and the like.

The event sources 102 generate event messages in response to clinical events and communicate the event messages to the event handler 106. Clinical events include one or more of physiological events, such as detection of low potassium in patients, notification of workflow items, such as a medication administration is due or overdue, system events, such as a redundant array of independent disks (RAID) failures, and the like.

The event messages include information pertaining to the associated clinical event that a clinician would find pertinent. For example, an event message generated in response to a blood pressure alert for a patient includes the blood pressure of the patient. Each of the event messages include one or more worklist items and one or more of a unique event identifier, capabilities, event properties, time properties, source properties, target properties, acknowledgement properties, and the like, discussed in detail below. A worklist item is an action to be performed in response to an event. The event messages are communicated in one or more of a one-way mode, a two-way mode, or the like. Messages communicated in the one-way mode do not require responses; whereas, messages communicated in the two-way mode require responses. In certain embodiments, responses can be used by the event sources 102 to trigger actions in the event sources 102.

In some embodiments, a distinction is made between one-way event sources and two-way event sources. One-way event sources include the ability to send messages, but not receive messages; and, two-way event sources include the ability to send and receive messages, such as a user response to an alert. Thus, two-way event sources send one-way messages and/or two-way messages and receive messages; whereas, one-way event sources only send one-way messages.

Additionally or alternatively, in some embodiments, a distinction is be made between subscribed event sources and unsubscribed event sources. Subscribed events sources support a standardized protocol 105 understood by the event handler 106, by which they communicate directly with the event handler 106. Unsubscribed event sources, in contrast to subscribed event sources, lack support for the standardized protocol 105 understood by the event handler 106, whereby they communicate indirectly with the event handler 106.

The event source interfaces 104 bridge communications between unsubscribed event sources and the event handler 106. The event source interfaces 104 receive messages sent from the unsubscribed event sources to the event handler 106, reformat the messages into the standardized protocol 105 supported by the event handler 106, and forward the reformatted messages to the event handler 106. Further, the event source interfaces 104 receive messages sent in the standardized protocol 105 from the event handler 106 to the unsubscribed event sources, reformat the messages into a format accepted by the unsubscribed event sources, and forward the reformatted messages to the unsubscribed event sources.

The event source interfaces 104 suitably include a single event source interface for all unsubscribed event sources, an interface for or built into each unsubscribed event source, or the like. However, other configurations are contemplated. For example, an event source interface is employed for each type of unsubscribed event source (e.g., a Philips Intellivue™ monitor MX800).

The event source interfaces 104 advantageously ensure interoperability between the event sources 102 and the event handler 106. However, because the event source interfaces 104 need not be used by subscribed event sources and the messages sent in the standardized protocol 105 ensure interoperability, the messaging system 100 need not include the event source interfaces 104 when the messaging system 100 only communicates with subscribed event sources.

The event handler 106 receives inbound messages, such as event messages and/or response messages, from the event sources 102 and/or the event targets 112, and communicates outbound messages, such as escalation messages and/or event handler response messages, corresponding to the inbound messages to targets and the like. Inbound event messages from the event sources 102 suitably yield outbound escalation messages to the event targets 112 of the event messages, and inbound response messages from the event targets 112 suitably yield outbound event handler response messages to the event sources 102.

Upon receipt of an inbound message, the event handler 106 suitably verifies and, possibly, modifies the inbound message using one or more rules. A rule suitably includes a match criteria and a match action, which is carried out if the match criteria is met. The match action includes, for example, modifying the inbound message. The match action and/or the match criteria can take into account one or more of hospital policies, target settings, properties of the inbound message, on-call status, worklists, workflows, other events, and the like.

Figure 3:
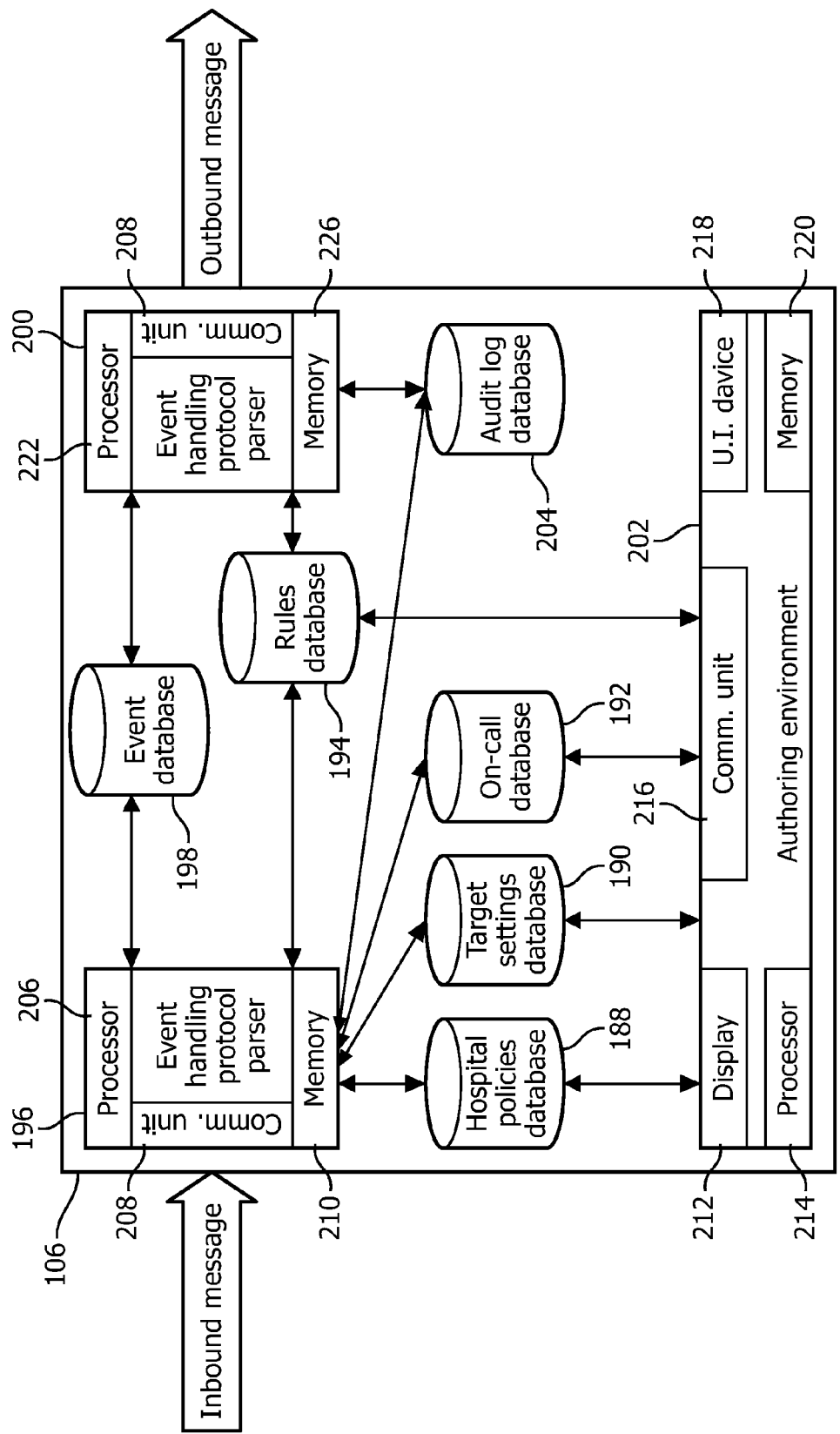
FIG. 3 is a block diagram of an event handler according to aspects of the present disclosure.

Further, upon receipt of the inbound message, the event handler 106 suitably adds the inbound message, with any modifications that may have been made to it, to an event database 198 (see FIG. 3). Each inbound message includes one or more worklist items. Therefore, the inbound message is added to the event database 198 by way of adding the worklist items to the database. A worklist item is an action to be performed in response to an event. For example, it is contemplated that a worklist item specifies that an alert about a patient's hypoglycemia is to be provided to the patient's doctor.

To send outbound messages, the event handler 106 suitably monitors worklist items in the event database 198 to determine which, if any, of the worklist items need an outbound message sent, determines when to send the message based on a number of factors, discussed below, and ultimately sends the message to the target user. Suitably, this is performed using one or more rules, where the match criteria specify the criteria for sending an outbound message and the match action specify how to send the outbound message. In one example, the rules include a rule generating an outbound message for worklist items specifying that an outbound message is a priority to be sent immediately for a target user. As another example, the rules include a rule for generating an outbound message for any worklist items that are overdue in the sense that an outbound message was previously sent and no response message has been received within an allowed amount of time.

The event handler 106 suitably communicates with one or more of the event source interfaces 104, the message service interface 108, subscribed event sources, and the like, using the standardized protocol 105, which provides a standardized format to represent all inbound and outbound messages. The standardized format is defined by one or more properties. In certain embodiments, the properties are arranged in a hierarchical structure. The properties include one or more of a unique event identifier, capabilities, event properties, time and/or escalation properties, source properties, target properties, acknowledgement properties, and the like.

The unique event identifier uniquely identifies each event to which a message relates. The unique event identifier allows the event handler 106 to determine an association between worklist items in the event database 198 and the message. For example, a two-way event message leads to the addition of a worklist item to the event database 198, where the worklist item is indexed using the unique event identifier of the event message. A response message then identifies an association with the worklist item using the unique event identifier.

The capabilities include, for example, properties of an event source or an event target for handling event messages or response messages, respectively. For example, capabilities include one or more of support for one-way event communications, support for two-way event communications, maintenance of local worklists, capability of providing choices encapsulated in the messages, support of visual messages, support of audio messages, and the like.

The event properties, for example, identify one or more of the type of event prompting generation of the message, the severity of the event, and the like. Event types include one or more physiological events, protocol events, workflow events, system events, status events, equipment events, and the like. Status events include events describing the status of a patient, a system, or the like and include one or more of unit status (e.g., active orphan equipment), system status (e.g., recorder out of paper), system health (e.g., RAID failure), quality assurance status (e.g., patient compliance is below the target of 60%), and the like. Further, event types are used to group events. For example, a nurse separates protocol reminders (e.g., draw lactate) from workflow reminders (e.g., vitals due) on a clinical information system. Event severity distinguishes high priority events (e.g., suspect sepsis) from low priority events (e.g., no data from sensor for 30 minutes).

The time and/or escalation properties include one or more of overdue time, escalation action, escalation time, delay properties, and the like for worklist items. Overdue time identifies the time that elapses before a worklist item is classified as overdue. Escalation action identifies how the worklist item is to be escalated. Escalation time identifies the time by when an associated worklist item needs to be escalated.

The delay properties specify how long a response to a worklist item may be delayed. The delay properties include one or more of a property for no delay, which includes, for example, a default for bed alerts, a property for the length of delay, a property defining the length of time an alert needs to be persistent or active in order to be processed by the system, and the like. The length of delay ranges from 0 (implying no delay) up to a predetermined number, such as 1440, with units of measure such as seconds or minutes. In certain embodiments, the property for the length of delay subsumes the property for no delay, where a length of delay of 0 implicates no delay. Additionally, or alternatively, in certain embodiments, the delay properties are substitutable to a predefined unit schedule (i.e., delay for this shift). Additionally, or alternatively, in certain embodiments, the delay is settable (when applicable) per each level of escalation. Additionally, or alternatively, in certain embodiments, for alerts subject to time based standards, the event source and/or event target are not allowed to select a delay.

The source properties typically include one or more of source type, one or more source parameters, source location, and the like. The source type identifies the type of event source (e.g., Philips Intellivue™ monitor MX 800). The source parameters identifies the type of parameters that triggered the event (e.g., blood pressure). The source location identifies where the source is located (e.g., Cardiology unit II).

The target properties typically include one or more of target user, target role, target alias, target application, and the like. The target user specifies an individual to which a message is directed (e.g., Dr. William Smith). The target role identifies the role of the target user (e.g., cardiologist on call or ICU nurse). The target alias identifies the target user if the name is not known (e.g., the patient's wife). The target application includes be a device (e.g., the Central station display, Beeper 4434, etc.).

The acknowledgement properties suitably capture the status of a worklist item. The acknowledgement properties include one or more of acknowledged (e.g., Dr. Smith acknowledged message), failed to send (e.g., message did not clear send queue), failed to receive (e.g., returned message from receiving service indicates fail), failed to acknowledge (e.g., received at end device but no user acknowledged the alert), forced rollover (e.g., user requested rollover), forced escalation (e.g., user requested escalation), and the like.

The standardized format divides inbound messages into one or more workflow items, which each include one or more properties. In certain embodiments, each workflow item is divided into one or more targets, which each include one or more properties. Additionally or alternatively, in certain embodiments, the standardized format includes a global section of one or more properties, where these properties are applied to each of the worklist items unless overridden by properties in the worklist items.

As should be appreciated in view of the preceding discussion, the standardized protocol 105 allows the event sources 102 to generate messages specifying the business logic for routing the messages. In turn, this allows the event sources 102 that utilize the standardized protocol 105 to establish a mechanism for the event handler 106 to pass the messages with an end user context as part of the message and have the end user response passed back to the event sources 102, without the event sources 102 needing to know anything about the end user's status or preferences.

The message service interface 108 bridges communications between the event handler 106 and the message service 110 in circumstances when the message service 110 lacks support for the standardized protocol 105 supported by the event handler 106. The message service interface 108 receives messages sent from the event handler 106 to the message service 110, reformats the messages into a communications protocol supported by the message service 110, and forwards the reformatted messages to the message service 110. Further, the message service interface 108 receives messages sent from the message service 110 to the event handler 106, reformats the messages into the standardized protocol 105 supported by the event handler 106, and forwards the reformatted messages to the event handler 106. When the message service 110 supports the standardized protocol 105 supported by the event handler 106, the message service interface 108 may be unnecessary and/or removed from the messaging system 100.

The message service 110 delivers escalation messages from the event handler 106 to the event targets 112 and/or response messages thereto to the event handler 106. Further, in certain embodiments, the message service 110 keeps track of users logged on to the message service 110. As with the event sources 102, the message service 110 can be characterized as subscribed or unsubscribed depending upon whether it supports the standardized protocol 105 supported by the event handler 106.

The event targets 112 receive escalation messages from the event handler 106 and, in some embodiments, generate and communicate response messages to the event handler 106. Response messages, like event messages, include one or more worklist items. Typically, to generate a response message, an event target presents an event message on a display and/or prompts a user of the event target to provide a response thereto via the display and/or a user input device. Of interest to note, an escalation message for an event message may be sent to multiple event targets 112 at once. The user response and ability to respond may be different depending on the event target. The response messages include, for example, one or more of a unique event identifier, capabilities, event properties, time properties, source properties, target properties, acknowledgement properties, and the like, as discussed above. As with the event sources 102, in some embodiments, a distinction is made between one-way event targets and two-way event targets. Additionally or alternatively, in some embodiments, a distinction is made between subscribed event targets and unsubscribed event targets.

Figure 2:
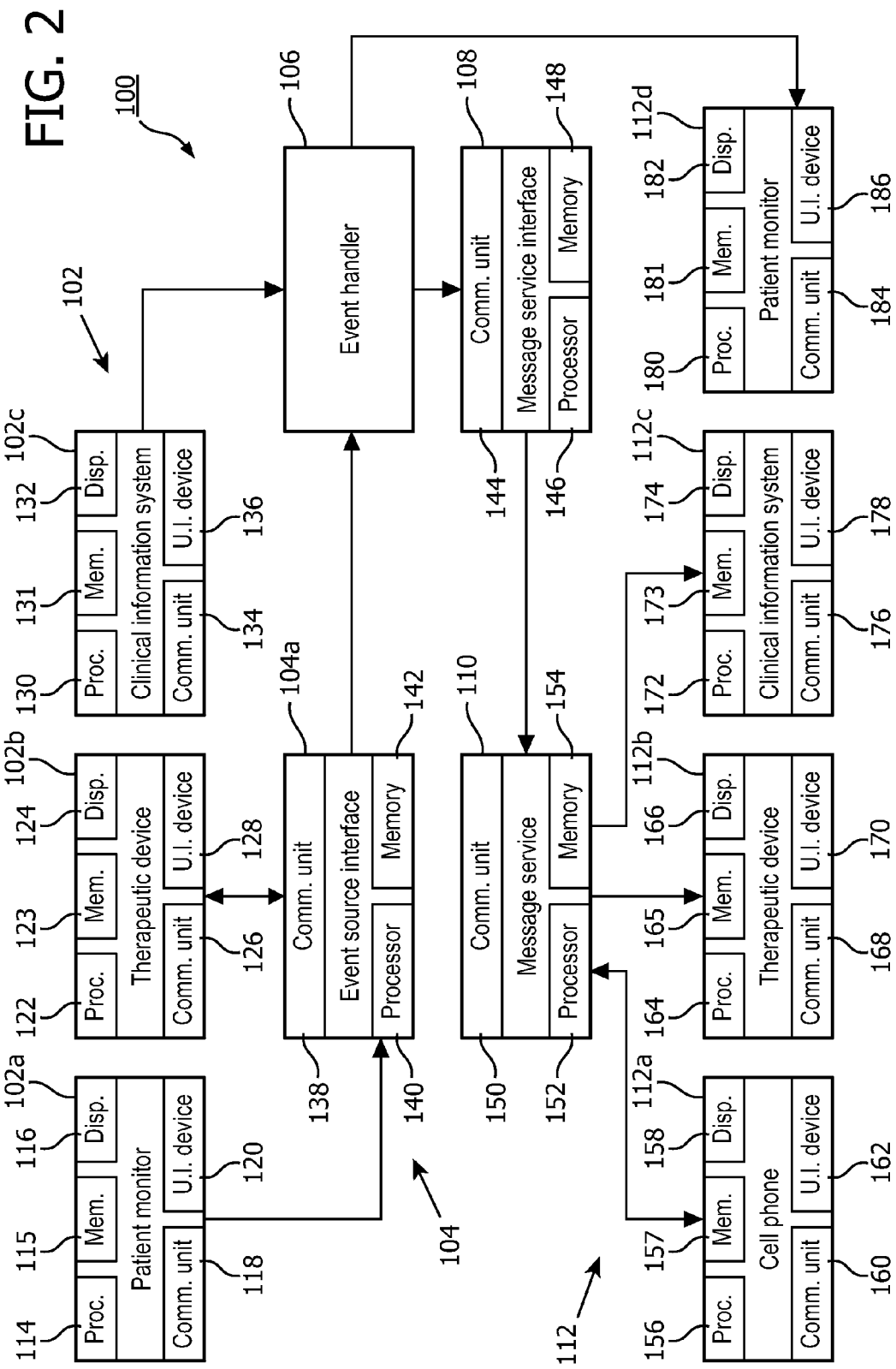
FIG. 2 is a detailed block diagram of the messaging system of FIG. 1.

With reference to FIG. 2, the event sources 102, in the illustrated embodiments, include one or more of monitors, such as a patient monitor 102a, clinical decision support applications, therapeutic devices, such as a therapeutic device 102b, clinical information systems, such as a clinical information system 102c, and the like.

Communication units 118, 126, 134 of the event sources 102 facilitate communication between the event sources 102 and external devices, such as the event handler 106 and/or the event source interfaces 104. Suitably, communication is performed by way of one or more communications networks. Memories 115, 123, 131 of the event sources 102 store patient data and the like and/or store executable instructions for performing one of more of the functions associated with the event sources 102. Displays 116, 124, 132 of the event sources 102 allow the event sources 102 to display data and/or messages for the benefit of users at the respective one of the event sources 102. User input devices 120, 128, 136 of the event sources 102 allow users of the event sources 102 to interact with the associated event source 102 and/or respond to messages displayed on its display. Processors and/or controllers 114, 122, 130 of the event sources 102 execute instructions stored on the memories to carry out the functions associated with the event sources 102.

The event source interfaces 104 in the illustrated embodiments include a first event source interface 104a, which interfaces with multiple event sources. Communication units 138 of the event source interfaces 104 facilitate communication between an associated event source interface and an external device, such as the event handler 106 and the event source 102. Memories 142 of the event source interfaces 104 store executable instructions for performing one of more of the functions associated with the event source interfaces 104. Processors and/or controllers 140 of the event source interfaces 104 execute instructions stored on the memories to carry out the functions associated with the event source interfaces 104. The memories 142, in some embodiments, store or buffer the data or messages from the event sources 102.

Further, each of the event source interfaces 104 suitably communicates via one or more communications networks. For example, in certain embodiments, an event source interface communicates with an unsubscribed event source via a first communications network and the event handler 106 via a second communications network, where the first communications network is different than the second communications network.

The event handler 106 communicates with the event targets 112 via the message service interface 108 and/or the message service 110, and communicates with the event sources 102 directly or via the event source interface 104. In certain embodiments, the event handler 106 additionally, or alternatively, communicates with the event targets 112 directly.

The message service interface 108 in the illustrated embodiments includes one or more of a communications unit 144, a processor and/or controller 146, a memory 148, and the like. The communications unit 144 facilitates communication between the message service interface 108 and an external device, such as the message service 110 and the event handler 106. The memory 148 stores executable instructions for performing one of more of the functions associated with the message service interface 108. The processor and/or controller 146 executes instructions stored on the memory 148 to carry out the functions associated with the message service interface 108.

The message service interface 108 suitably communicates via one or more communications networks. For example, in certain embodiments, the message service interface 108 receives an escalation message from the event handler 106 via a first communicate network and forward the escalation message to the message service 110 via a second communications network.

The message service 110 in the illustrated embodiment includes one or more of a communications unit 150, a processor and/or 152, a memory 154, and the like. The communications unit 150 facilitates communication between the message service 110 and one or more of the message service interface 108, the event handler 106, the event targets 112, and the like. Suitably, this is by way of one or more communications networks. The memory 154 stores executable instructions for performing one of more of the functions associated with the message service 110. The processor and/or controller 152 executes instructions stored on the memory 154 to carry out the functions associated with message service 110.

The event targets 112 in the illustrated embodiments include one or more of hand held devices, such as a cell phone 112a, therapeutic devices, such as a therapeutic device 112b, clinical information systems, such as a clinical information system 112c, monitors, such as a patient monitor 112d, clinical decision support applications, and the like. Further the event targets 112 include one or more one-way event targets and/or one or more two-way event targets. Additionally, the event targets include one or more subscribed event targets and/or one or more unsubscribed event targets, depending on whether or not the event targets support the standardized protocol 105.

Communication units 160, 168, 176, 184 of the event targets 112 facilitate communication between the event targets 112 and external devices, such as the event handler 106 and the message service 110. Communications are suitably conducted using one or more communications networks. Memories 157, 165, 173, 181 of the event targets 112 store one or more of patient data, executable instructions for performing one of more of the functions associated with the event targets 112, and the like. Displays 158, 166, 174, 182 of the event targets 112 allow the event targets 112 to display data and/or messages for the benefit of users of the event targets 112. User input devices 162, 170, 178, 186 of the event targets 112 allow users of the event targets 112 to interact with the event targets 112 and/or respond to messages displayed on the displays. Processors and/or controllers 156, 164, 172, 180 of the event targets 112 execute instructions stored on the memories to carry out the functions associated with the event targets 112.

The event handler 106 illustrated in FIG. 3 includes one or more of a hospital policies database 188, a target settings database 190, an on-call database 192, a rules database 194, an event handling protocol parser 196, the event database 198, an authoring environment 202, an event handling rules executor 200, an audit log database 204, and the like. Although depicted with the event handler 106, the various databases in some embodiments can be central, institution, or department wide databases that are accessed by the event handler 106.

The hospital policies database 188 includes one or more settings allowing hospital administrators to specify hospital policy. These settings, for example, let hospital administrators specify the minimum severity level for physiological events received from the event sources 102. The hospital policies are suitably applied to inbound messages via one or more rules in the rules database 194. In certain embodiments, the hospital policies include hard policies and soft policies. Hard policies are blocked from being modified and/or overwritten by other settings, such as target settings; whereas, soft policies may be overwritten by other settings, such as target settings.

The target settings database 190 includes one or more settings specific to a target of an inbound message. For example, the target settings allow an individual to specify how they are contacted, such as via a cell phone only. These settings are suitably applied so long as they do not conflict with hard hospital policies. Targets can include one or more of event sources, event targets, individuals, roles, aliases, applications, devices, and the like. As with hospital policies, target settings are suitably applied to inbound messages via one or more rules in the rules database 194. In certain embodiments, the target settings are linked to preset communication profiles, such as a paging interface, central stations, and unit bound clients.

The on-call database 192 tracks those clinicians who are presently on-call and typically includes one or more on-call records specifying clinicians currently on-call. In certain embodiments, the on-call records include the roles of clinicians. For example, the on-call database 192 includes an on-call record specifying that Joe Smith is currently on call with oncology. One or more of the authoring environment 202, the message service 110, and the like may update the on-call records.

The rules database 194 includes one or more rules for verifying and/or modifying worklist items in inbound messages and/or the event database 198. The rules for verifying and/or modifying worklist items in inbound messages are applied by the event handling protocol parser 196, and the rules for verifying and/or modifying worklist items in the event database 198 are applied by the event handling rules executor 200. As noted above, a rule suitably includes a match criteria and a match action, where the match action is carried out if the match criteria is met. A match action includes, for example, escalating a worklist item, modifying a worklist item in an inbound message and/or the event database 198, and the like.

In certain embodiments, the rules include one or more rules to verify and/or modify worklist items on the basis of one or more specified targets. These rules use the on-call database 192 to verify that an individual specified as a target in a worklist item is on-call or reachable, and, if not, to replace the individual specified as the target with one who is on-call or reachable. Additionally, or alternatively, these rules use the on-call database 192 to replace a target role specified as a target for a worklist item with an individual who is on-call. In both cases, the target is replaced according to one or more properties contained in the worklist item, hospital policies, target settings, and the like.

Additionally or alternatively, in certain embodiments, the rules include one or more rules to verify and/or modify worklist items on the basis of worklists. A worklist, for example, includes one or more tasks that need to be performed, such as providing a Pneumovax vaccine prior to discharging a critically ill patient. Worklists are comprised of various worklist items in an inbound message and/or the event database 198. Worklists are often specific to one or more of targets in a worklist item, such as an event source or an event target, patients, target roles, target individuals, and the like.

Among other things, it is contemplated that the rules making use of worklists in the illustrated embodiment can increase and/or decrease the priority of worklist items based on the worklists. This is accomplished through modification of the severity of a worklist item, the response time for a two-way worklist item, and the like. For example, a rule could cause the event handling protocol parser 196 to increase an overdue time for a worklist item in an inbound message if a target thereof becomes overwhelmed with a more severe event. Hence, in a sense, the worklist items associated with a worklists are dynamically ranked, where this ranking is adjusted using the rules.

Additionally or alternatively, in certain embodiments, the rules include one or more rules to verify and/or modify worklist items on the basis of source, such as the event sources 102 or the event targets 112. For example, while an interface, such as the event source interfaces 104 or the message service interface 110, allows a target to parse a message from an unsubscribed source, the message could still lack certain essential information. These rules add information and/or modify existing information of worklist items sent from unsubscribed sources to fill any voids that exist. Typically, these rules are only applied by the event handling protocol parser 196.

Additionally or alternatively, in certain embodiments, the rules include one or more rules to verify and/or modify worklist items on the basis of workflows. Workflows are suitably specific to events or specific to targets, such as an event source, an event target, patients, target roles, target individuals, and the like. In some embodiments, the workflows include state machines defining the workflows. Further, in some embodiments, the rules delay outbound messages for a worklist item until an associated workflow reaches a particular state.

Additionally or alternatively, in certain embodiments, the rules include one or more rules to verify and/or modify worklist items on the basis of hospital policies, target settings, or the like. For example, the rules include one or more rules augmenting worklist items of a particular event type so the worklist items include a minimum severity level. As another example, the rules include one or more rules augmenting worklist items directed to a target individual so as to contact said individual using a means of communication preferred by the individual, such as via a cell phone.

The rules database 194 further includes one or more rules for escalating worklist items in the event database 198. These rules are applied by the event handling rules executor 200. Escalation refers to sending an outbound message to a target, whether it is an event target or an event source. For example, a rule specifies that an escalation message should be provided to a second target if a first target does not acknowledge a previously provided escalation message within 30 minutes. As another example, a rule specifies that an event handler response message should be communicated to an event source every 5 minutes for at most 60 minutes until delivery is successful.

The event handling protocol parser 196 processes inbound messages, including event messages and/or response messages, to extract the one more worklist items contained therein. Suitably, the event handling protocol parser 196 is employed to parse inbound messages in the format of the standardized protocol 105. Therefore, a number of properties, including one or more of unique event identifier, capabilities, event properties, target properties, acknowledgement properties, and the like, define the worklist items.

The event handling protocol parser 196 further verifies and, when appropriate, updates extracted worklist items. The extracted worklist items are verified and/or modified using one or more rules from the rules database 194, where the rules are applied using one or more of hospital policies, target settings, properties of the inbound message, on-call status, worklists, workflows, other events, and the like. The extracted and, potentially, updated worklist items are then stored in the event database 198.

The event handling protocol parser 196 includes one or more of a processor 206, a communication unit 208, a memory 210, and the like. The communications unit 208 in the illustrated embodiment facilitates communication between the event handling protocol parser 196 and other devices, such as the event source interfaces 104, the event sources 102, the hospital policies database 188, and the like. Communications are suitably performed via one or more communications networks. The memory 210 stores executable instructions for performing one of more of the functions associated with the event handling protocol parser 196. The processor 206 executes instructions stored on the memory 210 to carry out the functions associated with the event handling protocol parser 196.

The event database 198 stores extracted and, potentially, updated worklist items. The worklist items are suitably defined according to the standardized protocol 105. Therefore, the event database 198 stores one or more of a unique event identifier, capabilities, event properties, target properties, response properties, and the like.

The authoring environment 202 allows authorized users to modify one or more of hospital policies, target settings, and rules in the hospital policies database 188, the target settings database 190, and the rules database 194, respectively. In certain embodiments, the authoring environment 202 further allows authorized users to modify the on-call records of the on-call database 192. For example, the authoring environment 202 allows an authorized user to change the roles of clinicians. In other embodiments, data interfaces with external scheduling systems are used to directly and automatically update the user role and on-call database 192. The authoring environment 202 is also important for generating rules to update messages from unsubscribed sources, such unsubscribed event sources, an unsubscribed message service, and unsubscribed event targets. This enables messages from unsubscribed sources to be handled in the same fashion as those from subscribed event sources. In certain embodiments, the authoring environment 202 is sandboxed or locally replicated from the production system so rules can be tested and verified without interfering with the active configuration, and then activated to the production system.

A desktop computer, a computer server, and the like suitably embody the authoring environment 202. Both distributed and localized computer services are contemplated. The authoring environment 202 includes one or more of a display 212, a processor and/or controller 214, a communication unit 216, a user interface device 218, a memory 220, and the like. The communications unit 216 facilitates communication between the authoring environment 202 and other components of the event handler 106, such as the hospital policies database 188, the target settings database 190, the on-call database 192, and the rules database 194. Communications are suitably performed via one or more communications networks. The memory 220 stores executable instructions for performing one of more of the functions associated with the authoring environment 202. The processor and/or controller 214 executes instructions stored on the memory 220 to carry out the functions associated with the authoring environment 202. The user input device 218 and the display 212 allow users of the authoring environment 202 to interact with the constituent database of the event handler 106.

The event handling rules executor 200 queries the event database 198 to determine if there are worklist items that need to be acted upon using the rules in the rules database 194. A worklist item needs to be acted upon if an outbound messages needs to be sent therefor. For example, if a worklist item specifies it requires immediate delivery to a target, the worklist needs to be acted upon. Suitably, the event handling rules executor 200 checks for worklist items that need to be acted upon in regular intervals. However, other trigger events are contemplated. For example, in certain embodiments, each worklist item is appropriated its own timer to trigger a check of the worklist item.

When the event handling rules executor 200 identifies one or more worklist items that need to be acted upon, it verifies the worklist items and generates an outbound message for the worklist items in the standardized format 105, using one or more rules in the rules database 194. Outbound messages include escalation messages and event handler response messages. These rules suitably verify and/or generate the worklist items on the basis of one or more of hospital policies, target settings, properties of the inbound message, on-call status, worklists, workflows, other events, and the like. The generated outbound messages are then sent to the event target or event source specified by the worklist item, depending upon the source of the worklist items (i.e., event message or response message).

After an outbound message is sent for a worklist item, the event handling rules executor 200 removes the worklist item from the event database 198 or updates it in the event database 198 to reflect that an outbound message was sent. The worklist item is suitably removed from the event database 198 when the tasks associated therewith are completed, so as to maintain the event database 198 with only the pending worklist items. A worklist item for a one-way event message is suitably completed when an escalation message is delivered to the event target, and a worklist item for a two-way event message is suitably completed when a response message to the event message is delivered to the event source of the event message. Typically, response messages are one-way.

The event handling rules executor 200 includes one or more of a processor and/or controller 222, a communication unit 224, a memory 226, and the like. The communications unit 224 facilitates communication between the event handling rules executor 200 and other devices, such as the message service interface 108, the event targets 112, the rules database 194, and the like. Communications are suitably performed via one or more communications networks. The memory 226 stores executable instructions for performing one of more of the functions associated with the event handling rules executor 200. The processor and/or controller 222 executes instructions stored on the memory 226 to carry out the functions associated with the event handling protocol parser 200.

The audit log database 204 maintains a log of the steps taken by the event handling protocol parser 196 and the event handing rules executor 200. Suitably, all steps are logged, but more sophisticated logging schemes are amenable. Logging all steps allows authorized users to reconstruct past event messages that have been removed from the event database 198.

Figure 4:
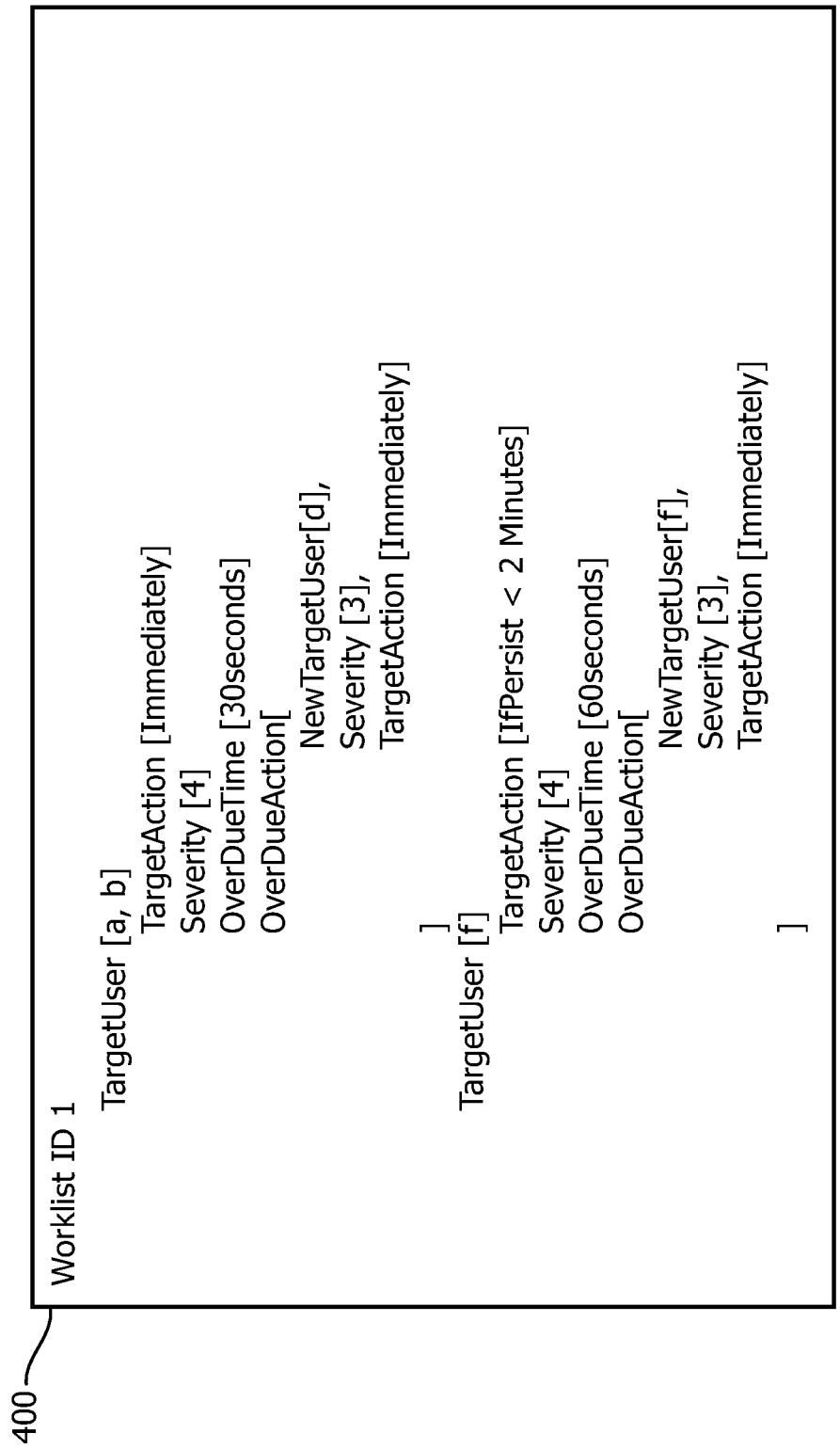
FIG. 4 is an event message according to aspects of the present disclosure.

With reference to FIG. 4, an example of an event message 400 generated by, for example, a patient monitor is illustrated. The event message 400 employs the standardized protocol 105, described of above, and is directed to multiple targets. For example, the event message 400 is directed to users a and b, which need to acknowledge an escalation message at a severity level "4" within 30 seconds of delivery; otherwise, the event message 400 is escalated for immediate notification at a severity level "3" to user d. The event message 400 is further directed to user f at a severity level "3" only if the event persists more than 2 minutes. User f would have to acknowledge the alert within 60 seconds, so as not to be notified again.

Figure 5:
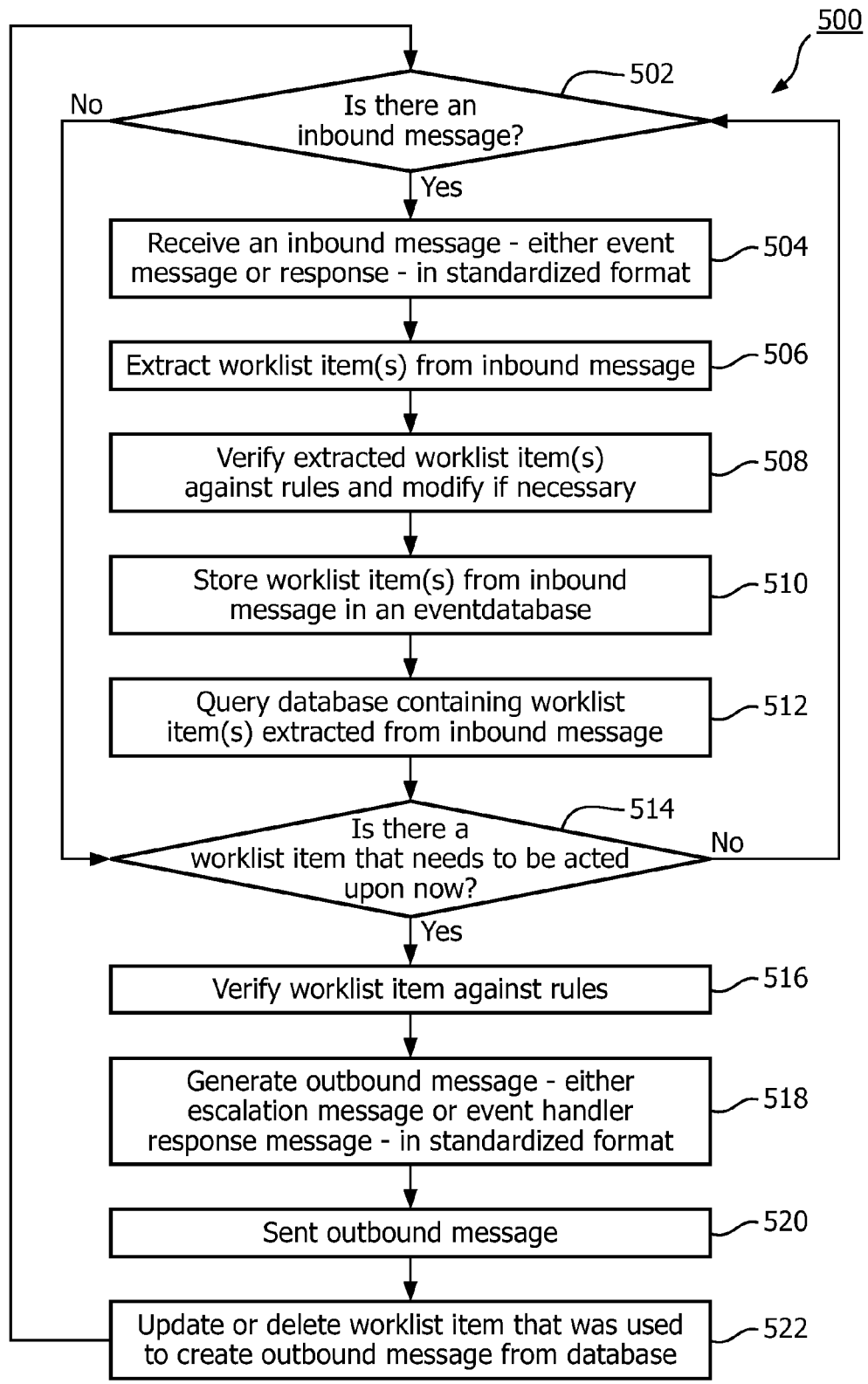
FIG. 5 is a block diagram for a method of routing clinical messages.

With reference to FIG. 5, a method 500 of routing clinical messages using the event handler 106 of FIG. 1 is provided. A determination 502 is made as to whether an inbound message, either an event message or a response message, is present. If no inbound message is present, the event database 198 is queried 512 and a determination 514 is made as to whether a worklist item therein needs to be acted upon. If an inbound message is present, it is received 504 in the standardized format 105. Worklist items contained in the inbound message are extracted 506. The extracted worklist items are verified and, possibly, modified 508 using one or more rules in the rules database 194. These rules are, for example, based on one or more of hospital policies, target settings, properties of the event messages, on-call status, worklists, workflows, other events, and the like. The verified and, possibly, modified rules are then stored 510 in the event database 198. The event database 198 is queried 512 and a determination 514 is made as to whether a worklist item therein needs to be acted upon. This determination is suitably made using one or more rules in the rules database 194. If no worklist items are determined to need action, the determination as to whether an inbound message is present 502 is repeated. Suitably, a delay is interposed. If a work list item is identified that needs action, the worklist item is verified 516 against one or more rules in the rules database 194 and an outbound message, either an escalation message or an event handler response message, is generated 518 and sent 520 in the standardized format 105 to a target user identified by the rules. The worklist item is then updated or deleted 522. Method 500 then starts again with determination 502.

Figure 6:
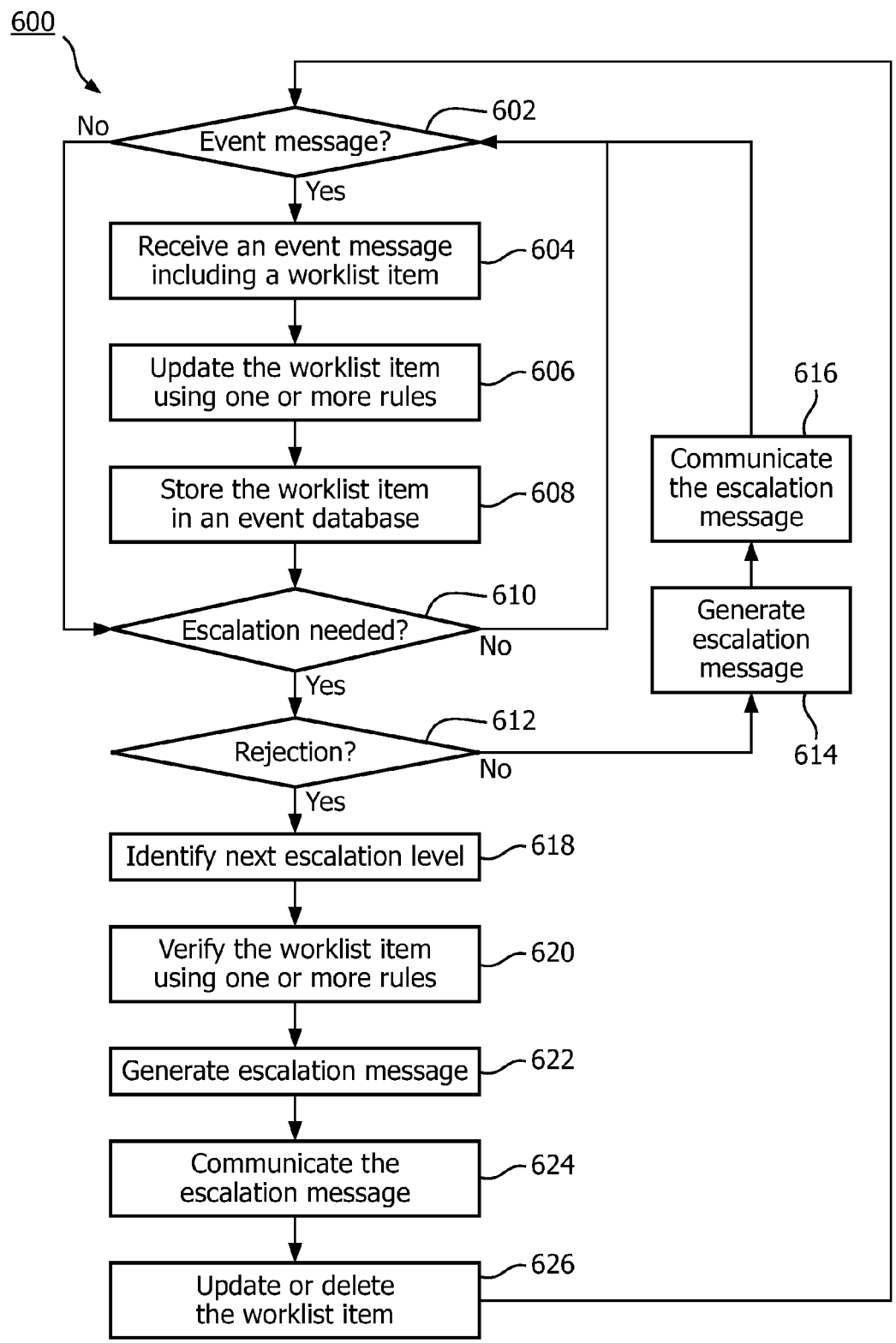
FIG. 6 is a block diagram for a method of escalating work list items based on target availability; and, FIG. 7 is a block diagram for a method of self describing and communicating event information.

With reference to FIG. 6, a method 600 of escalating worklist items based on target availability is provided. The method 600 is one embodiment of the method 500 and is suitably performed by the processors 206, 214, 222 of the event handler 106. As will be seen hereafter, the method 600 advantageously allows worklist items for a location, device, or patient, such as a bed, to be more quickly serviced by refraining from alerting targets known to be servicing higher priority worklist items. Further, the method 600 advantageously reduces alarm fatigue and distraction on the part of the targets, thereby improving overall safety. For ease of discussion, the method 600 is limited to a single worklist item. However, it is to be appreciated it is equally amenable to a plurality of worklist items and event messages.

The method 600 presupposes one or more of the databases 188, 190, 192, 194, 198, 204 of the event handler 106 cooperate to define escalation sequences and assignments thereof for locations, devices, or patients of an institution employing the event handler 106. Each of the escalation sequences includes one or more escalation levels and the order escalation advances through the escalation levels. For example, a location, device, or patient includes an escalation sequence identifying a first escalation level of primary targets and a second escalation level of secondary targets, where escalation proceeds from the first escalation level to the second escalation level.

The method 600 further presupposes one or more of the databases 188, 190, 192, 194, 198, 204 of the event handler 106 cooperate to define location, device, or patient assignments for targets, such as users, groups, devices, and so on, and escalation level assignments for the location, device, or patient assignments. For example, a first user is assigned to a first escalation level of a patient, and a second user is assigned to a second escalation level of the patient. Stated differently, the first user is assigned primary responsibility for the patient, and the second user is assigned secondary responsibility for the patient.

A determination 602 is made as to whether an event message, including a worklist item, for a location, device, or patient is present. If no event message is presented, a determination 610 is made as to whether escalation is needed, as discussed below. Otherwise, the event message is received 604 from an event source 102, such as a patient monitor, optionally in the standardized format. The location, device, or patient is assigned an escalation sequence including a plurality of escalation levels, each escalation level including a target, such as a user, a device, an application, a group, and so on. As noted above, escalation sequence and assignments are suitably defined through cooperation of one or more of the databases 188, 190, 192, 194, 198, 204 of the event handler 106. The worklist item includes a current position within the escalation sequence. The current position is initially the first escalation level of the escalation sequence, but advances with escalation.

After receiving 604 the worklist item, it is optionally updated 606 (i.e., verified and modified) using one or more rules in the rules database 194. These rules are, for example, based on one or more of hospital policies, target settings, properties of the event messages, on-call status, worklists, workflows, other worklist items, and the like. For more detail, attention is directed to the foregoing discussion of the event handler 106. The verified and, possibly, modified worklist item is then stored 608 in the event database 198.

The determination 610 is next made as to whether a worklist item needs escalation (i.e., that an escalation message needs to be sent) by querying the event database 198 and checking the worklist item against one or more rules in the rules database 194. For example, a rule may specify a first escalation message is to be sent immediately upon receipt of the worklist item, and another rule may specify a second escalation message is to be sent after a predetermined period of time lapses without receipt of any acceptance and/or acknowledgment of the first escalation message. As another example, a rule may specify that if a previously sent escalation message for the worklist item is rejected by the target, then escalation is in order. Typically, the event database 198 is queried periodically, but it is also contemplated that the event database 198 is queried continuously or upon the happening of an event.

In some embodiments, when the worklist item is to be escalated, a determination 612 is made as to whether a target of the first escalation level of the escalation sequence previously rejected a worklist item with a priority level higher or equal to a priority level of the worklist item to be escalated. Optionally, the previous rejection is limited to a rejection within a predetermined period of time from the determination 612. It is contemplated that the predetermined period can be specific to the target and, optionally, specified in the target settings database 190. When such a rejection has not been made and an escalation message for the worklist item has not been sent to the target, an escalation message is generated 614 and communicated 616 to the target of the first escalation level. The determination 610 of whether a worklist item is to be escalated is then repeated after the determination 602 as to whether a new event message is present is made.

When it is determined the worklist item is to be escalated and, if applicable, the rejection has been made, the event handler identifies 618 a next escalation level of the location, device, or patient. This includes retrieving the escalation sequence for the location, device, or patient corresponding to the event message, as well as the location, device, or patient assignments for the targets and escalation level assignments for the location, device, or patient assignments, from one or more of the databases 188, 190, 192, 194, 198, 204 of the event handler 106. Advantageously, by retrieving the assignments for each escalation, changes in escalation sequences and/or targets assigned to escalation levels (e.g., due to schedule changes or shift changes) are taken in to account. When an escalation sequence does not exist, a default escalation sequence including at least one escalation level can be employed. The escalation level can include, for example, supervisors or managers of the institution.

Beginning with the current position within the escalation sequence, the escalation levels of the retrieved escalation sequence are then stepped through in order until the end of the escalation sequence is reached or an escalation level with a target that is not already servicing a higher and/or equal priority worklist item is found. While stepping through the escalation sequence, the current position is updated. In some embodiments, the next escalation level includes at least one target not already servicing a higher priority and/or equal priority worklist item and not already servicing a worklist item exceeding a predetermined priority threshold. For example, if a primary target is servicing a severe, but not life critical, worklist item and a life critical worklist item for the primary target is received, the received worklist item can be escalated to a secondary target.

A target is deemed to be servicing a worklist item when a message accepting and/or acknowledging the worklist item is received from the target. Further, a target is deemed to have finished servicing a worklist item upon receipt of a message to that effect and/or after a predetermined period of time from the acceptance and/or acknowledgement has lapsed. In some embodiments, the predetermined period is specific to the target and, optionally, specified in the target settings database 190. Further, in some embodiments, a target is deemed to have finished servicing a worklist item upon receipt of a message indicating the target wishes to pass the worklist item to another target via the escalation procedure. For example, a primary target for a location, device, or patient receives a high priority worklist item for a location, device, or patient and failed to finish a low priority worklist item for another location, device, or patient for which it is the primary target. The low priority worklist item can be passed to a secondary target. The event handler 106 suitably tracks whether targets are servicing worklist items by maintaining records thereof in one of the databases 188, 190, 192, 194, 198, 204 and/or the memories 210, 226, 220 of the event handler 106.

When the end of the escalation sequence is reached, a default escalation sequence can be employed. Otherwise, the worklist item is verified 620 against one or more rules in the rules database 194 and an escalation message for the worklist item is generated 622 and communicated 624 to the identified target via an event target 112. Suitably the escalation message is sent in the standardized format. The worklist item is then deleted or updated 626 to reflect the escalation message was sent, and the determination 602 is made as to whether new event messages are present. In some embodiments, lower priority worklist items the identified target is servicing are escalated in response to the identified target servicing the worklist item. It is contemplated that this escalation can further require receipt of a message from the identified target indicating the at least one identified target wishes to pass the lower priority worklist items to other targets via the escalation procedure. Further, it is contemplated that escalation can be to a target, such as a supervisor, chosen by the identified target.

In some embodiments, priorities of worklist items being serviced by the identified target are compared against a predetermined priority threshold. Notably, these worklist items are of a lower priority than the received worklist item because the identified target would otherwise not receive an escalation message for the worklist item. In response to these worklist items exceeding the predetermined priority threshold, the escalation message is also communicated to targets of the escalation level following the next escalation level. For example, if a target was sent an escalation message for a serious, but not critical worklist item, and a life critical worklist item is received for the target, an escalation message for the life critical worklist item can be sent to the target, as well as another target in the higher escalation level.

Figure 7:
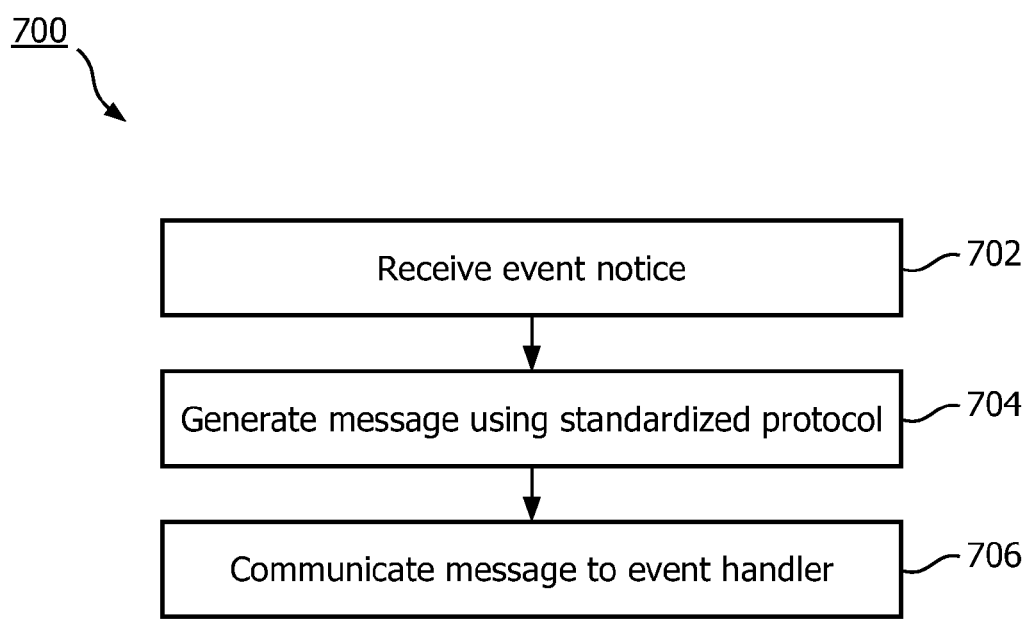

With reference to FIG. 7, a method 700 of self-describing and communicating event information to the event handler 106 is provided. One of the event source interfaces 104 and/or the message service interface 108 suitably performs the method 700. Event information, such as a notice of an event or a user response to an event, is received 702 from, for example, one of the event sources 102 and/or the message service 110. A message is generated 704 using the standardized protocol 105. The message includes the event information and one or more worklist items, represented using one or more standardized message properties. The worklist items specify to whom the message is directed and how the message should be escalated by the event handler 106. The message is then communicated 706 to the event handler 106.

Each of the databases described herein, such as the hospital policies database 188, suitably include a computer database, where the computer database is embodied by a single computer, distributed across a plurality of computers, or the like. Further, each of the databases suitably stores data in a structured manner facilitating recall and access to such data. Further, as used herein, a memory includes one or more of a non-transient computer readable medium; a magnetic disk or other magnetic storage medium; an optical disk or other optical storage medium; a random access memory (RAM), read-only memory (ROM), or other electronic memory device or chip or set of operatively interconnected chips; an Internet server from which the stored instructions may be retrieved via the Internet or a local area network; or so forth. Further, as used herein, a controller includes one or more of a microprocessor, a microcontroller, a graphic processing unit (GPU), an application-specific integrated circuit (ASIC), a field-programmable gate array (FPGA), and the like; a communications network includes one or more of the Internet, a local area network, a wide area network, a wireless network, a wired network, a cellular network, a data bus, such as USB and I2C, and the like; a user input device includes one or more of a mouse, a keyboard, a touch screen display, one or more buttons, one or more switches, one or more toggles, voice driven interaction, and the like; and a display includes one or more of a LCD display, an LED display, a plasma display, a projection display, a touch screen display, and the like.

The teachings of the present disclosure may be deployed in any clinical IT infrastructure (both in-patient and out-patient), where there are devices (e.g., monitors) and information systems (e.g., ICU information systems or healthcare information systems) that generate alerts or reminders. In systems that are able to expose clinical worklists, the present disclosure can extract that information and consolidate and maintain it.

Additionally, the teachings of the present disclosure may be deployed outside of healthcare. For example, they may be employed for use in hospitality management, such as room service or food service. As another example, they may be employed for use with avionics and marine multisystem event management where workflow consolidation across multiple systems is needed.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

Having thus described the preferred embodiments, the invention is now claimed to be:

1. A messaging system for routing clinical messages, said messaging system comprising:
an event handler comprising:
a memory with executable instructions stored thereon; and
a processor configured to access said memory to execute said instructions and to:
receive one or more inbound messages, including one or more worklist items, from one or more event sources;
store the worklist items in an event database; and,
generate and communicate outbound messages for one or more worklist items in the event database that need to be acted upon, as determined by one or more rules; and
a standardized protocol to represent the inbound messages and the outbound messages;
wherein the event handler verifies and/or modifies the worklist items of the inbound messages using one or more rules, wherein the rules are based on one or more of hospital policies, target settings, properties of the inbound messages, on-call status, worklists, and workflows.

2. The messaging system according to claim 1, wherein the event handler determines the worklist items that need to be acted upon using one or more rules, wherein the rules include one or more rules based on worklists implicit in the event database and/or workflows.

3. The messaging system according to claim 1, wherein the event handler updates and/or deletes worklist items in the event database for which outbound messages were generated and communicated.

4. The messaging system according to claim 1, wherein the inbound messages include properties specifying when corresponding outbound messages are to be sent.

5. The messaging system according to claim 1, wherein the event handler is configured to:
receive a worklist item for a location, device, or patient from the inbound messages, wherein the location, device, or patient includes an escalation sequence of escalation levels, each escalation level including a target;
determine whether the worklist item is to be escalated using the rules;
in response to determining the worklist item is to be escalated, identify a next escalation level of the location, device, or patient, the next escalation level including only target(s) not already servicing higher and/or equal priority worklist items; and,
generate and communicate an outbound message for the worklist item to the identified target.

6. The messaging system according to claim 5, wherein the next escalation level is identified by stepping through escalation levels of the escalation sequence until an escalation level including a target not already servicing higher and/or equal priority worklist items is found.

7. A method of routing clinical messages, said method performed by one or more processors preprogrammed to perform said method, said method comprising:
receiving one or more inbound messages in a standardized protocol from one or more event sources, said inbound messages including one or more worklist items;
storing the worklist items in an event database;
generating and communicating outbound messages in the standardized protocol for one or more worklist items in the event database that need to be acted upon, as determined by one or more rules;
receiving a worklist item for a location, device, or patient from the inbound messages, wherein the location, device, or patient includes an escalation sequence of escalation levels, each escalation level including a target;
determining whether the worklist item is to be escalated using the rules;
in response to determining the worklist item is to be escalated, identifying a next escalation level of the location, device, or patient, the next escalation level including only target(s) not already servicing higher and/or equal priority worklist items; and generating and communicating an outbound message for the worklist item to the identified target.

8. The method according to claim 7, further including:

verifying and/or modifying the worklist items of the inbound messages using one or more rules, wherein the rules are based on one or more of hospital policies, target settings, properties of the inbound messages, on-call status, worklists, and workflows.

9. The method according to claim 7, wherein the generation of the outbound messages use one or more rules based on one or more of hospital policies, target settings, properties of the inbound messages, on-call status, worklists, and workflows.

10. The method according to claim 7, wherein the identifying includes:

stepping through escalation levels of the escalation sequence until an escalation level including a target not already servicing higher and/or equal priority worklist items is found.

11. A computer readable medium carrying software which controls one or more processors to perform the method according to claim 8.

12. A method of self-describing and communicating event information to an event handler, comprising one or more processors, said method performed by one or more processors preprogrammed to perform the method, said method comprising:

receiving event information including a notice of an event and/or a user response to the notice of an event;

generating a message using a standardized protocol, wherein the message includes the event information and one or more worklist items, represented using one or more standardized message properties, wherein the worklist items specify to whom the message is directed and how the message should be routed by the event handler; and, communicating the message to an event handler;

wherein the event handler verifies and/or modifies the worklist items of the inbound messages using one or more rules, wherein the rules are based on one or more of hospital policies, target settings, properties of the inbound messages, on-call status, worklists, and workflows.

13. The method according to claim 12, wherein each of the worklist items specify one or more targets for all or a subset of the event information.

14. The method according to claim 12, wherein the message includes business logic for how all or a subset of the event information should be routed.

15. The method according to claim 12, further including:

receiving second event information including a user response to the notice of the event;

generating a second message using the standardized protocol, the second message including the second event information and specifying to whom the second message is directed and how the second message should be routed by the event handler; and, communicating the second message to the event handler.

* * * * *